United States Patent [19]

DeCicco et al.

[11] Patent Number: 5,443,987
[45] Date of Patent: Aug. 22, 1995

[54] DETECTION SYSTEM FOR MICROBIAL CONTAMINATION IN HEALTH-CARE PRODUCTS

[76] Inventors: Benedict T. DeCicco, 12505 Caswell La., Bowie, Md. 20715; James K. Keeven, 1215 N. Fort Myer Dr., #305, Arlington, Va. 22209

[21] Appl. No.: 115,543
[22] Filed: Sep. 2, 1993
[51] Int. Cl.⁶ ............. C12N 1/00; C12Q 1/00; C12Q 1/02
[52] U.S. Cl. ............. 435/4; 435/29; 435/31; 435/732; 435/968; 436/172; 436/1
[58] Field of Search ............. 435/4, 29, 31, 7.32, 435/968; 436/172, 201, 1; 514/844–848, 873, 900, 901, 902, 969, 827, 828, 880, 881, 912, 944, 945

[56] References Cited

U.S. PATENT DOCUMENTS 4,812,393  3/1989  Goswami et al. ............. 435/4
4,847,066  7/1989  Honigs et al. ............. 424/7.1
5,047,331  9/1991  Swaine et al. ............. 435/31

*Primary Examiner*—Michael G. Wityshyn
*Assistant Examiner*—Jane Williams
*Attorney, Agent, or Firm*—Whitham, Curtis, Whitham & McGinn

[57] ABSTRACT

An in-situ microbial contaminant detection system provides a chemical reagent within a liquid health care product or in close association with product packaging containing the health care product. The chemical reagent interacts with a variety of microbial contaminants or byproducts, such as enzymes and acids, of the microbial contaminants that are commonly found in health care products (e.g., P. cepacia, S. marcescens, E. cloacae, E. gergoviae, E. aerogenes, K. pneumoniae, and P. aeruginosa) and provides a visible indication of microbial contamination that can readily be discerned by a consumer. A color change is preferred.

18 Claims, 1 Drawing Sheet

DETECTION SYSTEM FOR MICROBIAL CONTAMINATION IN HEALTH-CARE PRODUCTS

BACKGROUND OF THE INVENTION

1. Field of the Invention

This invention is related to a detection system which provides a visible indication readily discernible by a person (consumers, quality assurance/quality control personnel, etc.) that a health care product has become contaminated by microbial organisms. More particularly, the invention is directed to a detection system which can be positioned in-situ in the health care product or be associated with the health care product packaging, such that microbial contamination can be detected without the use of external test equipment or laboratory facilities.

2. Description of the Prior Art

Microbial contamination is a major problem with consumer health care products such as nasal sprays, contact lens solutions, medication, shampoos, lotions, etc. Many microorganisms pose a significant health hazard. If a health care product is contaminated, a consumer may unexpectedly inoculate himself or herself with a harmful bacterium, virus, fungus, or the like, simply by using the product as is directed (e.g., washing contact lenses in a contaminated cleansing solution, inspiring a nasal spray, etc.). Once inoculated, the consumer may experience minor difficulties such as skin or eye irritation, infection, inflammation, as well as significantly worse problems such as blindness, destruction of nasal cells, vomiting, diarrhea, etc. In view of these potential dangers, many techniques have been developed for detecting-microbial contamination.

U.S. Pat. No. 3,206,317 to Golber discloses a system for detecting food spoilage wherein packaging line personnel wipe food samples on an indicator disc during packaging operations. The indicator disc may include nutrient culture media and a chemical reagent that changes color to indicate that a product is contaminated. In operation, pH changes or oxidation-reduction changes produced by bacteria which are wiped on the disc will cause the chemical reagent to change color.

U.S. Pat. No. 4,242,447 to Findl discloses a process for the rapid detection of bacteria in liquid samples. In operation, an inducing agent is added to a liquid medium to cause the production of a particular enzyme in bacteria that may be present therein. The enzyme reacts with a fluorescent conjugate that is ingested by the bacteria to produce a detectable signal.

U.S. Pat. No. 4,556,636 to Belly et al. discloses a composition for detecting bacteria in biological fluids such as urine and blood that includes a glucose substrate and a dye which is reduced and undergoes a color change when incubated in admixture with bacteria.

U.S. Pat. No. 4,812,393 to Goswami et al. discloses a detection process where dyes are used in assays for microorganisms. The dyes may be attached to blocking groups and can react with hydrolytic enzymes or cells containing the enzymes.

U.S. Pat. No. 4,874,695 to Pincus discloses that yeasts and other microorganisms can be detected by culturing samples containing the microorganisms, and then detecting whether microorganisms have been stimulated to produce particular enzymes.

U.S. Pat. No. 4,906,565 to Vossen discloses a bioluminescent assay which detects microbial nucleotides.

U.S. Pat. No. 5,004,682 to Roberts et al. discloses a method for detecting microorganisms in chlorine or bromine treated water wherein a lysing agent is added to the water and, if microorganisms are present, single stranded target nucleic acid molecules released from the lysed cells are detected.

U.S. Pat. No. 5,073,488 to Matner et al. discloses a method for determining the performance of a sterilization cycle. Matner et al. contemplate detecting the presence of enzymes which are produced by microorganisms to determine whether sterilization was performed correctly.

U.S. Pat. No. 5,093,235 to Williams et al. discloses an immuno-dye reagent and assay for the detection of endotoxin. The detection system utilizes anti-endotoxin antibodies.

Many of the detection systems described above are complex and require that the tests be performed in a laboratory. These type of detection schemes are only suitable for quality control at a packaging plant. While quality control at a packaging plant is important, products can become contaminated after shipping, but prior to consumer usage or during consumer usage. Hence, despite production quality controls, there is still a danger that the end-user can be accidentally exposed to harmful contaminants from a product that outwardly appears to be safe. Therefore, there is a need for a detection system which can be easily used and understood by a consumer at the product's point of use.

Furthermore, health care products are different from other consumable items such as food and water, and are different from biological fluids such as urine and blood. The type of microorganisms that survive and proliferate in a health care product such as a nasal spray or contact lens solution are typically quite different from those which might be a contamination problem in apple juice or might be identified in a blood sample. Chemical reagents which may identify one type of microorganism in one medium may not be suitable for identifying other microorganisms in another type of medium. In addition, many chemical reagents will only detect one type of microorganism, and are not useful for detecting a broad spectrum of microbial contaminants. In view of this, there is a need for detection schemes which are suitable for identifying a wide variety of the types of microorganisms that would be likely contaminants in health care products.

SUMMARY OF THE INVENTION

It is an object of this invention to provide a microbial contamination detection system for health care products that is positioned in-situ or is closely associated with the health care product packaging that provides a visible change easily detected by consumers or the like when the health care product has become contaminated by microorganisms.

It is another object of this invention to select chemical compounds for incorporation into a health care product which will not interact adversely with the product, but which will be acted upon by a wide variety of microbial contaminants to provide a visibly detectable indication that the health care product is contaminated by microorganisms.

It is yet another object of this invention to provide an in-situ microbial contamination detection system that remains functional for extended periods of time.

According to the invention, indicator compounds that undergo a visible change after exposure to microorganisms or byproducts of microorganism contamination, such as enzymes produced by microorganism contaminants and the like, are provided in situ in health care products or are closely associated with the health care product packaging. The consumer, or any other individual that handles the health care product, can readily determine the presence or absence of microbial contamination simply by observing the visible change. The indicator compounds can be colorimetric reagents that are colorless in solution but decompose to a colored product upon being exposed to microbial contaminants. In addition, colorimetric reagents can be employed that are a first color when the product is uncontaminated and a second color when the product becomes contaminated (e.g., the product is blue in an uncontaminated condition but changes to pink once the product becomes contaminated). However, many other indicator compounds could also be employed including phosphorescent, fluorescent, chemiluminescent compounds, and redox compounds. The indicator compounds must be acted upon by the types of microbial contaminants which are commonly found in health care products. In some applications, multiple indicator compounds can be employed to detect the presence of a wide spectrum of microbial contaminants. The indicator compounds can be either hydrophilic or hydrophobic depending on the nature of the product (aqueous or emulsion), and can be dissolved in the product or be in solid form. In some applications, the indicator compound can be positioned within a semi-permeable membrane positioned within the health care product.

BRIEF DESCRIPTION OF THE DRAWINGS

The foregoing and other objects, aspects and advantages will be better understood from the following detailed description of the preferred embodiments of the invention with reference to the drawings, in which.

DETAILED DESCRIPTION OF THE PREFERRED EMBODIMENTS OF THE INVENTION

The invention contemplates combining an indicator compound with a health care product to allow a consumer to quickly determine whether the product has become contaminated with microorganisms. The indicator compound may be present in-situ in the health care product or may be closely associated with the health care product packaging. The liquid health care products in which this invention can find utility are wide ranging and include consumer products such as eye drops, contact lens solutions, nasal sprays, oral sprays, medicine, lotions, shampoos, etc., and include medical and clinical products such as lavage fluids, dialysis fluids, sterile salines and dextrose solutions, etc.

If the indicator compound is to be dissolved in a liquid health care product, the indicator compound should be selected to be hydrophilic or hydrophobic depending on the nature of the product. For example, eye drops are aqueous in character; therefore, the indicator compound used must be hydrophilic. By contrast, shampoos and lotions are often organic emulsions, and for these products the indicator compound should be hydrophobic. The indicator compound might also be suspended as particles within the health care product, thereby avoiding solubility problems.

Particular applications wherein the indicator compound is associated with the packaging as opposed to being dissolved in the health care product include the following.

Figure 1:
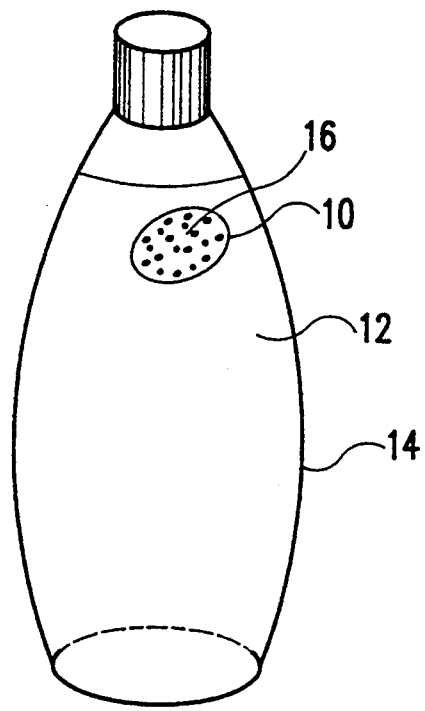
FIG. 1 is an isometric view of a bottle containing a liquid health care product with a semi-permeable membrane containing an indicator compound positioned therein.

First, it is contemplated that the indicator compound could be provided within a semipermeable membrane (e.g., dialysis tubing, etc.) that is placed in the health care product. For example, FIG. 1 shows a semipermeable bag 10 positioned within the liquid health care product 12 inside a bottle 14. The indicator compound 16 inside the bag 10 could be in either liquid or particulate form. The porosity of the semipermeable membrane would prevent the indicator compound 16 from being transferred to the health care product 12, but would allow enzymes or other constituents (acids, etc.) produced from microbial contaminants in the product to pass through the membrane, due to osmotic pressure or other transport mechanisms, and to interact with the indicator compound. The interaction would lead to a detectable color change or other visible change of the indicator compound within the semipermeable membrane that can easily be identified by the consumer.

Alternatively, the indicator compound, after it decomposes due to interaction with enzymes or the like, could be permitted to diffuse through the membrane into the health care product to provide a readily detectable visible change within the health care product. For example, the chemical reagent could be positioned inside a semi-permeable bag as a particulate and the membrane bag would be placed inside the bottle or other container holding the liquid health care product. After enzymes produced from microbial contaminants in the liquid health care product or the contaminants themselves pass through the semi-permeable bag, the particulate indicator would decompose to produce a colored or flourescent chemical which is free to diffuse into the health care product.

Figure 2:
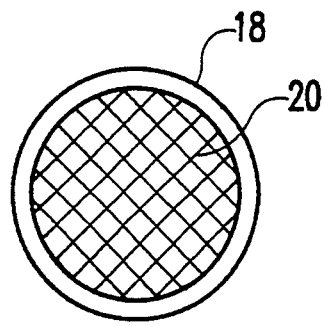
FIG. 2 is a plan view of a bottle cap with a fibrous material containing an indicator compound thereon.

Second, as shown in FIG. 2, the cap 18 of a bottle containing the health care product could be provided with a fibrous material 20 affixed inside, and the indicator compound would be immobilized on the fibrous material 20. The fibrous material 20 can be prepared from paper, porous particulate structures, cellulose, porous polymeric films, wood, glass fibers, woven or non-woven synthetic or non-synthetic fabrics, etc. U.S. Pat. No. 4,812,393 to Goswami et al., which is herein incorporated by reference, describes a number of support materials which could be used to support the indicator compounds of the present invention. By shaking the bottle or turning the bottle upside down, the consumer would bring the health care product into contact with the fibrous material. Microorganisms or microorganism byproducts such as enzymes that are present within the health care product would contact the immobilized indicator compound through the routine actions of the consumer, and this, in turn, would cause a visible change in the appearance that could readily be discerned by the consumer. For example, medication or other liquid health care products where the cap of a bottle needs to be unscrewed by the consumer prior to use would have a self-contained microbial contamination check throughout the storage life of the product. If the consumer unscrews the cap 18 and sees that the inside has changed color (red, etc.), he or she would know that the product has become contaminated and that they should purchase a new bottle.

Figure 3:
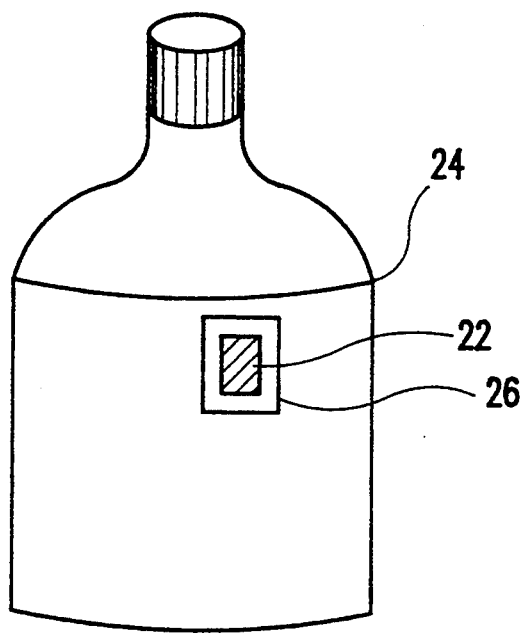
FIG. 3 is a side view of a health care product container which has a transparent window section for viewing an indicator compound immobilized on an inside surface thereof.

Third, as shown in FIG. 3, a solid-phase material 22, such as agarose, gelatin, polystyrene, polyesters (PET), polycarbonates, cellulose esters, etc., could be coated on the inside of the health product container 24 and the indicator compound would be immobilized on the solid-phase. The container would be provided with a transparent window 26 so that the consumer would be permitted to observe the solid-phase material 22. When the product becomes contaminated by microorganisms, the consumer would see a visible change in the appearance of the solid-phase material via the interaction of the microorganisms or byproducts of the microorganisms with the indicator compound positioned on the solid-phase material.

An advantage of some of the packaging ideas discussed above is that the indicator compound does not come into contact with the health care product. Therefore, the indicator compound would not pose any adverse health risks to the consumer. Furthermore, formulation of the health care product would not need to be altered. It should be understood that other mechanisms for having the indicator compound closely associated with the health care product packaging can be used within the practice of this invention. However, a chief requirement of this invention is that the consumer of the health care product does not need to perform any test to determine that the product is contaminated. For example, this invention is not directed to the use of test strips or discs external to the health care product where the user must sample the product, perform the test, and then observe a result on the strip or disc. Likewise, this invention does not require the user to perform a titration of a sample of the health care product or use electrodes or other laboratory equipment. Rather, this invention contemplates an arrangement where the consumer need only observe a visible change in the health care product or a visible change in a portion of the packaging which contains the health care product. No "experimenting" is required of the consumer.

The indicator compound should be present in the health care product or on the product packaging in a sufficient quantity for the user to observe a visible change once it is acted on by a microorganism or byproduct of a microorganism. It is envisioned that the total quantity of the indicator compound will be present at less than 10% by weight relative to the health care product. As is presented by the test data discussed below, indicator compounds can be chosen which are effective at concentrations as low as 0.01% weight in volume.

As discussed above, an important feature of this invention is that the consumer need not perform any testing prior to use of the product. Rather, he or she simply needs to observe whether or not a visible change in the health care product or in the indicator portion of the product packaging has occurred. Another important feature of this invention is that it provides a long-term product contamination check. Microbial contamination in medications, contact lens solutions, and other health care products which are used over a period of time may only emerge after several days, weeks or even months of use. Hence, by having an in-situ detection system the user will be assured that during the time period in which he or she is using a product, the product is free of microbial contamination.

A wide variety of microorganisms are known to contaminate health care products. The U.S. Pharmacopeia (USP) preservative effectiveness test identifies *Staphylococcus aureus*, *Eschericia coli* and *Pseudomonas aeruginosa* as standard "tester strains"; however, of these tester strains, only P. aeruginosa commonly occurs as a microbial contaminant in health care products. The main problem organisms for health care products include *Pseudomonas cepacia*, *Serratia marcescens*, *Enterobacter cloacae*, *Enterobacter gergoviae*, *Enterobacter aerogenes*, and *Klebsiella pneumoniae*. This invention is useful in detecting bacteria, fungi, and other microbial agents such as protozoans.

A series of experiments has been conducted to demonstrate the efficacy of an in-situ microbial detection system.

In the experiments, a wide variety of microbial strains were used. The microorganisms were grown overnight on Tryptic Soy Agar (TSA). Suspensions were made in 0.85% w/v saline to an optical density ($OD_{540}$) to yield between $9 \times 10^7$ and $3 \times 10^8$ colony forming units/milliliter (cfu/ml). 0.05 ml (50 µl) of the suspensions were inoculated into 5 ml of test solution in a borosilicate test tube. Test solutions included: (a) phosphate buffered saline (PBS) 0.25 M phosphate and 0.7% NaCl, (b) 0.85% NaCl w/v, and (c) an unpreserved contact lens solution which consisted of potassium phosphate buffer base plus eye comfort polymers. Chromogenic substrates (the indicator compounds) were added to the test solutions as a 1 in 100 dilution of 1% w/v in $H_2O$ or, if insoluble in water, as a powder.

In the experiments, the inoculated tubes were incubated in the dark at room temperature and inspected visually and spectrophotometrically at a wavelength of 400 nm for yellow color and 600 nm for blue color daily for 16 days and again after 30 days. Positives were determined visually. Table 1 identifies the indicator compounds used in the experiments and their characteristics.

TABLE 1

| Compound | Color Change | Water Solubility | Reactive Enzymes |
|---|---|---|---|
| p-nitrophenyl phosphate | Clear—>yellow | freely soluble | acid and alkaline phosphatases |
| p-nitrophenyl myristate | Clear—>yellow | insoluble | esterase |
| p-nitrophenyl laurate | Clear—>yellow | insoluble | esterase |
| p-nitrophenyl sulfate | Clear—>yellow | freely soluble | sulfatase |
| o-nitrophenyl B-D glucopyranoside | Clear—>yellow | freely soluble | B-D glucosidase |
| 5-bromo-3-chloro-3-indolyl-B-D glucopyranoside | Clear—>blue | insoluble | B-D glucosidase |

While Table 1 identifies six different colorimetric identifier compounds, it should be understood that there are literally hundreds of other colorimetric compounds which could be used within the practice of this invention. Other colorimetric compounds include 5-bromo-4- chloro-3-indolyl galactopyranoside, 5-bromo-4-chloro-3-indolyl glucopyranoside, 5-bromo-4-chloro-3-indolyl phosphate, 5-bromo-4-chloro-3-indolyl glucuronic acid, o-nitrophenyl beta-D-galactopyranoside, o-nitrophenyl beta-D-glucopyranoside, p-nitrophenyl phosphate, p-nitrophenyl myristate, 5-bromo-6-chloro-3-indolyl glucuronic acid, and 6-chloro-3-indolyl beta-D-glucuronic acid. In addition to colorimetric compounds, this invention could employ fluorometric, phosphorometric, and chemiluminescent compounds. Suitable fluorogenic compounds include fluorogenic 4-methylumbelliferyl derivatives (hydrolysable to 4-methylubelliferone), derivatives of 7-amido-4-methyl-coumarin (e.g., GB Patent No. 1,547,747 and European patent No. 0,000,063 to Agjinomoto both patents being herein incorporated by reference), diacetylfluoroscein derivatives, and fluorescamine. U.S. Pat. No. 5,073,488 to Matner et al. lists a wide variety of fluorogenic compounds and chromogenic compounds which can be used in the practice of this invention and that patent is herein incorporated by reference. Reducible and hydrolyzable dyes, including fluorescent dyes such as those described in U.S. Pat. No. 4,812,393 to Goswami et al. which is herein incorporated by reference, can be used within the practice of the invention. For example, fluorescent dyes can include coumarins, fluorescein derivatives, phenalenones, benzphenalenones, spiroacridines, and umbelliferone derivatives. Suitable chemiluminescent compounds include enzymatically cleavable 1,2 dioxetane compounds such as 3-(2'-spiroadamantane)-4-methoxy-(3''-phosphoryloxy)phenyl-1,2-dioxetane disodium salt. Selection criteria for the indicator compound can include the organisms to be detected, the nature of the health care product in which the indicator compound will be used, and the position in the health care product where the indicator compound will be located. The compounds discussed in Table 1 are all acted upon by various enzymes which may be produced by microbial contaminants; however, it should be understood that microbial contaminants could produce other constituents (acids, bases, etc.) which could be used to trigger a visible change in an indicator compound positioned in-situ in a health care product or an indicator compound closely associated with the product packaging.

Table 2 shows the date color development was observed in test solutions containing phosphate buffered saline at pH 7 that were inoculated with various microorganisms when the indicator compounds of Table 1 where positioned in-situ. The inoculum ranged from $9 \times 10^5$ to $3 \times 10^6$ cfu/ml and the indicator compound was present at 0.01% w/v.

TABLE 2

Indicator Compound
(1) p-nitrophenyl phosphate (turns yellow)
(2) p-nitrophenyl myristate (turns yellow)
(3) p-nitrophenyl laurate (turns yellow)
(4) p-nitrophenyl sulfate (turns yellow)
(5) o-nitrophenyl B-D-glucopyranoside (turns yellow)
(6) 5-bromo-3-chloro-5-indolyl-B-D-glucopyranoside (turns blue)

NC = no change

| Organism | (1) | (2) | (3) | (4) | (5) | (6) |
|---|---|---|---|---|---|---|
| uninoculated control | NC | NC | NC | NC | NC | NC |
| S. aureus 6538 | 30 | NC | NC | NC | NC | NC |
| P. aeruginosa 9027 | 30 | 7 | 2 | 9 | NC | NC |
| C. albicans 10231 | NC | 30 | 30 | NC | NC | NC |
| P. cepacia 25416 | 2 | 11 | 10 | NC | 1 | 1 |
| E. coli 8739 | 30 | NC | NC | NC | 11 | NC |
| S. marcescens 48 | 3 | 3 | 1 | NC | 1 | 1 |
| E. cloacae 0414 | NC | NC | NC | NC | 4 | NC |
| E. gergoviae 13048 | 2 | NC | NC | NC | 3 | 1 |
| E. aerogenes AVL | 7 | NC | NC | NC | 2 | 2 |
| K. pneumoniae 23357 | 4 | NC | NC | NC | 3 | 2 |

PBS was used to represent an unpreserved buffered saline solution that would be a base formulation for many different aqueous products. Table 2 shows that the indicator compounds do not change color on their own over the thirty day test period in the uninoculated test solutions. By contrast, each of the inoculated test solutions resulted in color development with one or more of the indicator compounds. Therefore, the color change observed is a direct indication of product contamination by microorganisms.

Table 2 suggests that by providing a product with a mixture of indicator compounds such as PNP phosphate and ONP glucopyranoside, all of the microorganisms except C. albicans would be detected. The main problem organisms, P. cepacia, S. marcescens, E. cloacae, E. gergoviae, E. aerogenes, and K. pneumoniae would be detected within four days, and some as quickly as one day. Tester strains used in the USP preservative test such as E. coli, S. aureus, and P. aeruginosa, would require more time for detection, but would ultimately be detected using the combination of indicator compounds. These tester strains, with the exception of P. aeruginosa, are rarely encountered in health care product contamination. Table 2 shows P. aeruginosa could be detected by using PNP-laurate, for example, in as little as two days. Hence, this invention particularly contemplates the use of combinations of indicator compounds to identify a wide spectrum of microorganism contaminants. In selecting the indicator compounds for a given health care product, the types of contaminants which are the biggest problem for the product should be identified and indicator compounds which are acted upon by those particular microorganism contaminants should be chosen.

Table 2 illustrates the utility of both water soluble and insoluble compounds within the practice of the invention. Color development was observed with PNP phosphate, PNP sulfate and ONP glucopyranoside which are water soluble, and color development was also observed with PNP myristate, PNP laurate, and 5-bromo-3-chloro-3-indolyl B-D glucopyranoside which are all water insoluble. If a health care product formulator wished to make a product that initially contained no dissolved chromogenic indicator compounds, but which allowed release of the colored indicator into solution upon contamination, this would be feasible with all the tested organisms except E. cloacae and S.aureus using 5-bromo-3-chloro-3-indolyl-B-D-glucopyranoside and PNP laurate. As discussed above, other combinations of indicator compounds could be chosen to monitor microbial contamination.

Table 2 also demonstrates the ability to generate different colors (yellow and blue) with the same enzyme. Specifically, the two indicator compounds containing B-D glucopyranoside are acted upon by B-D-glucosidase to produce blue and yellow colors. Hence, if different color indications are desired, a combination of indicator compounds, each of which is acted on by the same enzyme, can be employed to produce the desired color to indicate microbial contamination.

Most health care products are not nutrient free as is the case with the PBS solutions discussed in conjunction with Table 2 above. Table 3 provides test results with PBS solutions identical to those described above in conjunction with Table 2, but which also include a trace amount of nutrient (0.01% tryptic soy broth (TSB)). The organisms and indicator compounds used are identical in Tables 2 and 3.

TABLE 3

Indicator Compound
(1) p-nitrophenyl phosphate (turns yellow)
(2) p-nitrophenyl myristate (turns yellow)
(3) p-nitrophenyl laurate (turns yellow)
(4) p-nitrophenyl sulfate (turns yellow)
(5) o-nitrophenyl B-D-glucopyranoside (turns yellow)
(6) 5-bromo-3-chloro-5-indolyl-B-D-glucopyranoside (turns blue)
NC = no change

| Organism | (1) | (2) | (3) | (4) | (5) | (6) |
|---|---|---|---|---|---|---|
| uninoculated control | NC | NC | NC | NC | NC | NC |
| S. aureus 6538 | 7 | NC | NC | NC | NC | NC |
| P. aeruginosa 9027 | 5 | 1 | 1 | 2 | NC | NC |
| C. albicans 10231 | NC | 16 | 2 | NC | NC | NC |
| P. cepacia 25416 | 1 | 3 | 3 | NC | 1 | 1 |
| E. coli 8739 | 3 | NC | NC | NC | 2 | 2 |
| S. marcescens 48 | 1 | 1 | 1 | NC | 1 | 1 |
| E. cloacae 0414 | 14 | NC | NC | NC | 1 | 1 |
| E. gergoviae 13048 | 1 | NC | NC | NC | 1 | 1 |
| E. aerogenes AVL | 1 | NC | NC | 4 | 1 | 1 |
| K. pneumoniae 23357 | 1 | NC | NC | NC | 1 | 1 |

Table 3 shows that the small amount of nutrient in the test solutions in all cases led to as rapid or a more rapid color change being elicited from the indicator compound. In addition, Table 3 shows that some microorganisms react with indicator compounds that they do not react with in PBS alone. For example, E. cloacae reacts with PNP phosphate and 5-bromo-3-chloro-3-indolyl-B-D-glucopyranoside in the presence of 0.01% TSB, but not in its absence. Also, in the presence of 0.01% TSB, all tested microorganisms, except C. albicans, can be detected with PNP phosphate alone. Table 3 also shows that most microorganisms can be detected with either water soluble or insoluble indicator compounds.

Table 4 provides results for selected microorganisms and indicator compounds in an unpreserved contact lens formulation. As described above, the inoculum ranged from 9×10⁵ to 3×10⁶ cfu/ml and the indicator compound was present at 0.01% w/v.

TABLE 4

Indicator Compound
(1) p-nitrophenyl phosphate (turns yellow)
(2) p-nitrophenyl myristate (turns yellow)
(3) o-nitrophenyl B-D-glucopyranoside (turns yellow)
NC = no change

| Organism | (1) | (2) | (3) |
|---|---|---|---|
| uninoculated control | NC | NC | NC |
| S. aureus 6538 | NC | NC | NC |
| P. aeruginosa 9027 | 2 | 5 | NC |
| C. albicans 10231 | NC | NC | NC |
| P. cepacia 25416 | 1 | 4 | 1 |
| E. coli 8739 | NC | NC | NC |
| S. marcescens 48 | 1 | 4 | 1 |

Table 4 shows the use of indicator compounds in-situ in a health care product (contact lens solution). The results demonstrate that contaminants that pose particularly difficult problems for this kind of product, which include P. cepacia, S. marcescens and P. aeruginosa, can be quickly and accurately detected using indicator compounds in the product. The speed of color change observed was faster than that seen in PBS alone. This indicates the presence of some nutrient in the lens solution and the ability of the nutrient to accelerate color change.

Table 5 shows that in saline supplemented with 0.01% TSB, all the tested microorganisms except C. albicans rapidly produced a yellow color from in-situ PNP phosphate.

TABLE 5

| Organism | p-nitrophenyl phosphate (0.01% w/v) |
|---|---|
| uninoculated control | NC |
| S. aureus 6538 | 4 |
| P. aeruginosa 9027 | 2 |
| C. albicans 10231 | NC |
| P. cepacia 25416 | 1 |
| E. coli 8739 | 1 |
| S. marcescens 48 | 1 |
| E. cloacae 0414 | 2 |
| E. gergoviae 13048 | 1 |
| E. aerogenes AVL | 1 |
| K. pneumoniae 23357 | 1 |

The increased speed of color development seen in Table 5 as compared with Table 3 is probably due to the presence of phosphate in the PBS used in the solutions discussed in conjunction with Table 3. Phosphate is known to cause inhibition of acid and alkaline phosphatase enzymes.

While the invention has been described in terms of its preferred embodiments, those skilled in the art will recognize that the invention can be practiced with modification within the spirit and scope of the appended claims.

We claim:

1. A product, comprising:
   a liquid health care product positioned within product packaging for containing said liquid health care product; and
   means for sensing the presence of microbial contaminants selected from the group consisting of C. albicans, P. cepacia, S. marcescens, E. cloacae, E.

gergoviae, E. aerogenes, K. pneumoniae, E. coli, S. aureus and P. aeruginosa within said liquid health care product and providing a visible indication of microbial contamination of the packaged product, said means for sensing being positioned inside said product packaging for containing said liquid health care product, said means for sensing responding to enzymes produced by said microbial contaminants and metabolic processes involving enzymes produced by said microbial contaminants.

2. The product of claim 1 wherein said means for sensing is a chemical reagent dissolved or dispersed within said health care product.

3. The product of claim 2 wherein said chemical reagent provides a color change as said visible indication of microbial contamination.

4. The product of claim 2 wherein said chemical reagent provides chemiluminescent, phosphorescent, or fluorescent light as said visible indication of microbial contamination.

5. The product of claim 1 wherein said means for sensing is a chemical reagent which is present in said health care product at a concentration less than 10% by weight.

6. The product of claim 1 wherein said means for sensing is a chemical reagent or mixture of two or more different chemical reagents which provide a visual indication for contamination of said liquid health care product by at least three different said microbial contaminants.

7. The product of claim 1 wherein said enzymes produced by said microbial contaminants are selected from the group consisting of glucosidases, esterases, sulfatases and phosphatases.

8. A product, comprising:
a liquid health care product positioned within product packaging for containing said liquid health care product; and
means for sensing the presence of microbial contaminants selected from the group consisting of C. albicans, P. cepacia, S. marcescens, E. cloacae, E. gergoviae, E. aerogenes, K. pneumoniae, E. coli, S. aureus, and P. aeruginosa within said liquid health care product wherein said means for sensing comprises a semi-permeable membrane filled with a chemical reagent which provides a visible indication of microbial contamination of the packaged-product, said semi-permeable membrane being positioned within said liquid health-care product inside said product packaging, said means for sensing responding to enzymes produced by said microbial contaminants and metabolic processes involving enzymes produced by said microbial contaminants.

9. The product of claim 8 wherein said semi-permeable membrane allows microbial contaminants or enzymes and other byproducts of microbial contamination to pass through, but prevents the passage of said chemical reagent.

10. The product of claim 8 wherein said semi-permeable membrane allows said chemical reagent to diffuse therethrough only after decomposition or other changes resulting from exposure to microbial contaminants or enzymes and other byproducts of microbial contamination.

11. The product of claim 8 wherein said chemical reagent provides a color change as said visible indication of microbial contamination.

12. The product of claim 8 wherein said chemical reagent provides chemiluminescent, phosphorescent, or fluorescent light as said visible indication of microbial contamination.

13. A product, comprising:
a liquid health care product positioned within product packaging for containing said liquid health care product; and
means for sensing the presence of microbial contaminants selected from the group consisting of C. albicans, P. cepacia, S. marcescens, E. cloacae, E. gergoviae, E. aerogenes, K. pneumoniae, E. coli, S. aureus, and P. aeruginosa within said liquid health care product wherein said means for sensing comprises a chemical reagent which provides a visible indication of microbial contamination of the packaged product and a means for immobilizing said chemical reagent on an inside surface of said packaging containing said health care product, said means for sensing responding to enzymes produced by said microbial contaminants and metabolic processes involving enzymes produced by said microbial contaminants.

14. The product of claim 13 wherein said means for immobilizing is a fibrous material.

15. The product of claim 14 wherein said fibrous material is positioned inside a cap for said packaging containing said health care product.

16. The product of claim 13 wherein said means for immobilizing is a stationary phase positioned on an inside surface of said packaging containing said health care product.

17. The product of claim 13 wherein said chemical reagent provides a color change as said visible indication of microbial contamination.

18. The product of claim 13 wherein said chemical reagent provides chemiluminescent, phosphorescent, or fluorescent light as said visible indication of microbial contamination.

* * * * *